United States Patent
Wellhöfer

(10) Patent No.: US 9,610,197 B2
(45) Date of Patent: Apr. 4, 2017

(54) AUTOMATIC MACHINE SETTINGS FOR CUSTOMIZED REFRACTIVE SURGERY

(71) Applicant: Wavelight Gmbh, Erlangen (DE)

(72) Inventor: Armin Wellhöfer, Schwaig (DE)

(73) Assignee: Wavelight GmbH, Erlangen (DE)

( * ) Notice: Subject to any disclaimer, the term of this patent is extended or adjusted under 35 U.S.C. 154(b) by 0 days.

(21) Appl. No.: 14/781,248

(22) PCT Filed: Jun. 14, 2013

(86) PCT No.: PCT/EP2013/062399
§ 371 (c)(1),
(2) Date: Sep. 29, 2015

(87) PCT Pub. No.: WO2014/198336
PCT Pub. Date: Dec. 18, 2014

(65) Prior Publication Data
US 2016/0081755 A1    Mar. 24, 2016

(51) Int. Cl.
*A61B 3/10* (2006.01)
*A61B 3/14* (2006.01)
(Continued)

(52) U.S. Cl.
CPC ............ *A61F 9/008* (2013.01); *A61B 3/0033* (2013.01); *A61B 3/0075* (2013.01); *A61B 3/0083* (2013.01); *A61B 3/132* (2013.01); *A61B 19/26* (2013.01); *A61B 90/20* (2016.02); *A61B 90/50* (2016.02); *A61B 90/60* (2016.02);
(Continued)

(58) Field of Classification Search
USPC ................................. 351/200–246
See application file for complete search history.

(56) References Cited

U.S. PATENT DOCUMENTS

2005/0028077 A1    2/2005  Wen et al.
2007/0236661 A1*  10/2007  Fukuma ................. A61B 3/102
                                                            351/205
(Continued)

FOREIGN PATENT DOCUMENTS

CA      2819455 C    9/2008
CA      2719801 A1  10/2009
(Continued)

OTHER PUBLICATIONS

Valcarcel; "Tighe Richardson use an operating microscope while performing cataract eye surgery to return sight to Marylin Kansi, a 12-year-old girl from Cotabat"; U.S. Navy photo; Jun. 7, 2008; XP002713237; retrieved from the internet: URL: http//commons.wikimedia.org/wiki/File.

*Primary Examiner* — Mohammed Hasan

(57) ABSTRACT

An ophthalmic apparatus includes a resting member configured to provide rest for a human patient, and an ophthalmic device configured to perform one or more procedures with respect to an eye of the patient resting on the resting member, where the one or more procedures include at least one of an eye-surgical, therapeutic and diagnostic procedure. The apparatus also includes a user interface device configured to receive log-in data from a user, and a controller configured to access stored user profile data based on the log-in data and configure one or more configurable components of the apparatus in accordance with the accessed user profile data.

15 Claims, 3 Drawing Sheets

Figure 1:
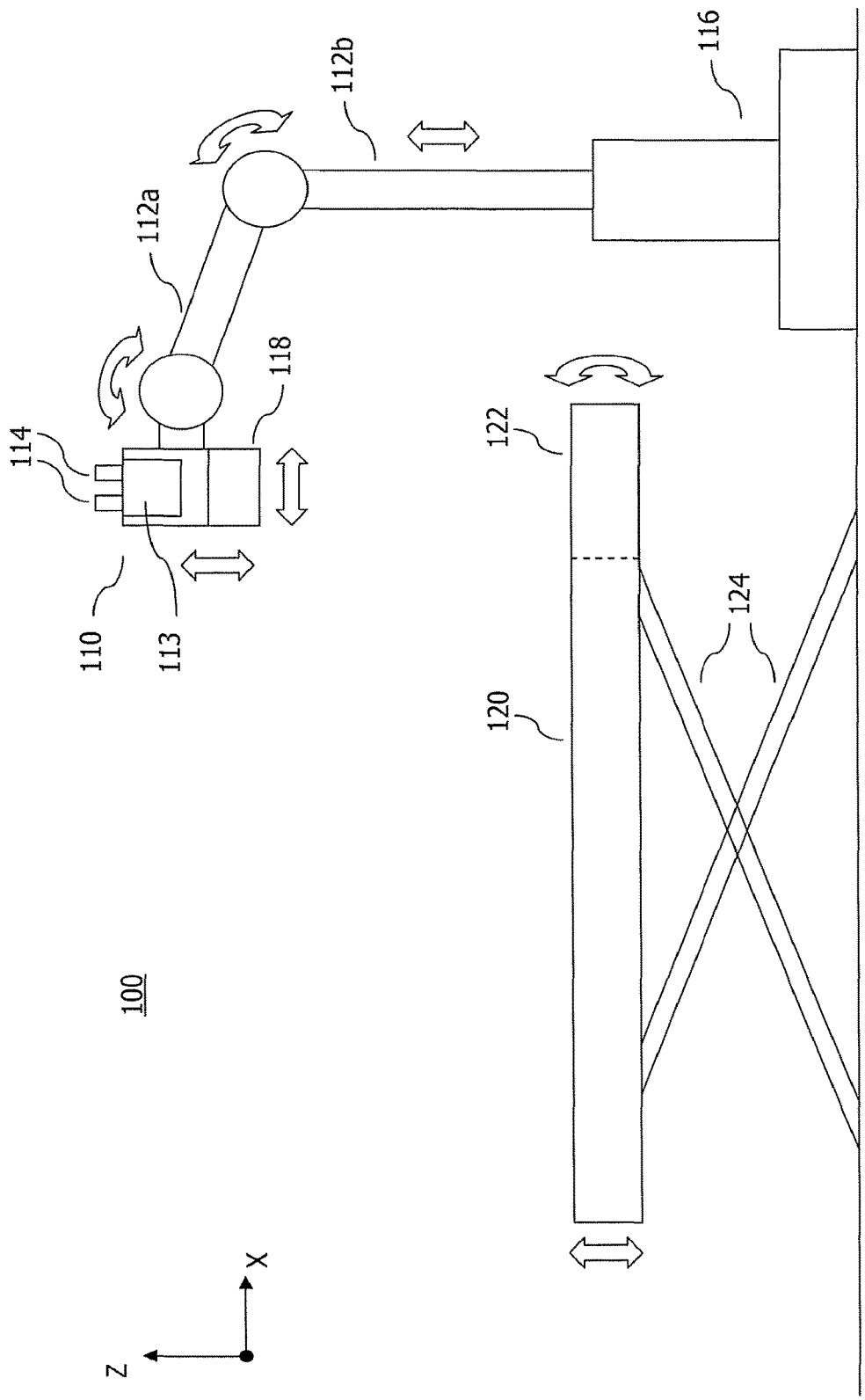

(51) Int. Cl.
  *A61B 3/00*    (2006.01)
  *A61F 9/008*   (2006.01)
  *A61G 13/02*   (2006.01)
  *A61B 3/13*    (2006.01)
  *A61B 19/00*   (2006.01)
  *A61B 90/50*   (2016.01)
  *A61B 90/60*   (2016.01)
  *A61B 90/20*   (2016.01)
  *A61F 9/00*    (2006.01)
  *A61G 12/00*   (2006.01)
  *A61B 90/14*   (2016.01)

(52) U.S. Cl.
  CPC .............. *A61G 13/02* (2013.01); *A61B 90/14* (2016.02); *A61F 9/00* (2013.01); *A61F 2009/00844* (2013.01); *A61G 12/007* (2013.01)

(56) References Cited

U.S. PATENT DOCUMENTS

2008/0044069 A1* 2/2008 DuGal .................. G06F 19/321
                                                    382/128
2008/0284979 A1   11/2008 Yee et al.
2009/0024799 A1    1/2009 Jahagirdar et al.
2012/0249956 A1* 10/2012 Narasimha-Iyer ..... A61B 3/102
                                                    351/206
2014/0112562 A1*  4/2014 Yamakawa ............ A61B 3/102
                                                    382/131

FOREIGN PATENT DOCUMENTS

| | | |
|---|---|---|
| CN | 1220592 A | 6/1999 |
| JP | 5253223 | 10/1993 |
| JP | H11-032983 | 2/1999 |
| JP | 2001-522257 | 11/2001 |
| JP | 2009-072369 | 4/2009 |
| JP | 2010-522002 | 7/2010 |
| JP | 003162335 | 8/2010 |
| JP | 2012-196238 | 10/2012 |
| KR | 10-2009-0080976 | 7/2009 |
| KR | 10-2010-0015565 | 2/2010 |
| KR | 10-2012-0138520 | 12/2012 |
| WO | 97/46184 | 12/1997 |
| WO | 2012/135073 A2 | 10/2012 |
| WO | 2013/000487 A1 | 1/2013 |

* cited by examiner

AUTOMATIC MACHINE SETTINGS FOR CUSTOMIZED REFRACTIVE SURGERY

CROSS REFERENCE TO RELATED APPLICATIONS

This application is a section 371 national stage phase of International Application No. PCT/EP2013/062399, filed 14 Jun. 2013, titled "AUTOMATIC MACHINE SETTINGS FOR CUSTOMIZED REFRACTIVE SURGERY", which is hereby incorporated by reference in its entirety.

The present invention relates to an ophthalmic apparatus comprising at least one configurable component and a controller for configuring the at least one configurable component in accordance with a stored user profile of a logged-in user.

BACKGROUND OF THE INVENTION

In the field of ophthalmology one or more ophthalmic devices are employed during eye-surgical, therapeutic and diagnostic procedures. While most of the devices can be adjusted for the patient, for example, a bed or chair for the patient can be moved up and down, the devices are not otherwise configurable.

SUMMARY OF THE DISCLOSURE

It is an object of embodiments of the present invention to provide an ophthalmic apparatus that provides improved handling and operation for the user.

In accordance with an aspect of the present invention, an ophthalmic apparatus comprises a resting member configured to provide rest for a patient, and an ophthalmic device configured to perform one or more procedures with respect to an eye of the patient resting on the resting member, where the one or more procedures include at least one of an eye-surgical, therapeutic and diagnostic procedure. The apparatus also comprises a user interface device configured to receive log-in data from a user, and a controller configured to access stored user profile data based on the log-in data and configure one or more configurable components of the apparatus in accordance with the accessed user profile data.

In an embodiment, the one or more configurable components include an illumination device, wherein the controller is configured to adjust the brightness of illumination light provided by the illumination device in accordance with the accessed user profile data.

In an embodiment, the one or more configurable components include one or more position-variable components, wherein the controller is configured to adjust a position of at least one of the one or more position-variable components in accordance with the accessed user profile data.

The position may include at least one of a horizontal position, a vertical position and an angular position.

In an embodiment, the one or more position-variable components include the resting member, where the resting member is variable for at least one of a height of a resting surface of the resting member, a horizontal position of the resting surface and an inclination of the resting surface. The controller may be configured to adjust at least one of the height, horizontal position and inclination of the resting surface in accordance with the accessed user profile data.

In an embodiment, the one or more position-variable components include one or more position-variable members of the ophthalmic device, wherein the controller is configured to adjust a position of at least one of the one or more position-variable members in accordance with the accessed user profile data.

In an embodiment, the ophthalmic device is equipped with a microscope having a pair of eyepieces, where at least one of the pair of eyepieces is position-variable with respect to the other eyepiece of the pair to vary the mutual distance between the pair. In this case the controller may be configured to adjust the mutual distance between the pair of eyepieces in accordance with the accessed user profile data.

In an embodiment, the ophthalmic device is equipped with a radiation emission head for emitting optical radiation toward the patient eye, wherein the radiation emission head is height-variable, and the controller is configured to adjust the height of the radiation emission head in accordance with the accessed user profile data. In an embodiment, the radiation emission head is height-variable relative to the resting surface of the resting member, and the controller is configured to adjust the height of the radiation emission head in relation to the resting surface in accordance with the accessed user profile data.

In accordance with another aspect of the present invention, a method of configuring an ophthalmic apparatus is disclosed. The ophthalmic apparatus includes at least a resting member providing rest for a human patient, an ophthalmic device for performing one or more procedures with respect to an eye of the patient resting on the resting member, the one or more procedures including at least one of an eye-surgical, therapeutic and diagnostic procedure, and a user interface device. The method comprises receiving log-in data from a user on the user interface device, accessing stored user profile data based on the log-in data, and configuring one or more configurable components of the ophthalmic apparatus in accordance with the accessed user profile data.

In an embodiment, the one or more configurable components include an illumination device, and the step of configuring comprises adjusting the brightness of illumination light provided by the illumination device in accordance with the accessed user profile data.

In an embodiment, the one or more configurable components include one or more position-variable components, and the step of configuring comprises adjusting a position of at least one of the one or more position-variable components in accordance with the accessed user profile data.

In an embodiment, the one or more position-variable components include the resting member, wherein the resting member is variable for at least one of a height of a resting surface of the resting member, a horizontal position of the resting surface and an inclination of the resting surface. In this embodiment, the step of configuring may comprise adjusting at least one of the height, horizontal position and inclination of the resting surface in accordance with the accessed user profile data.

In an embodiment, the one or more position-variable components include one or more position-variable members of the ophthalmic device, and the step of configuring comprises adjusting a position of at least one of the one or more position-variable members in accordance with the accessed user profile data.

In an embodiment, the ophthalmic device is equipped with a radiation emission head for emitting optical radiation toward the patient eye, wherein the radiation emission head is height-variable. In this embodiment, the step of configuring may comprise adjusting the height of the radiation emission head in accordance with the accessed user profile data and/or adjusting the height of the radiation emission head in relation to the resting surface of the resting member in accordance with the accessed user profile data.

Figure 2:
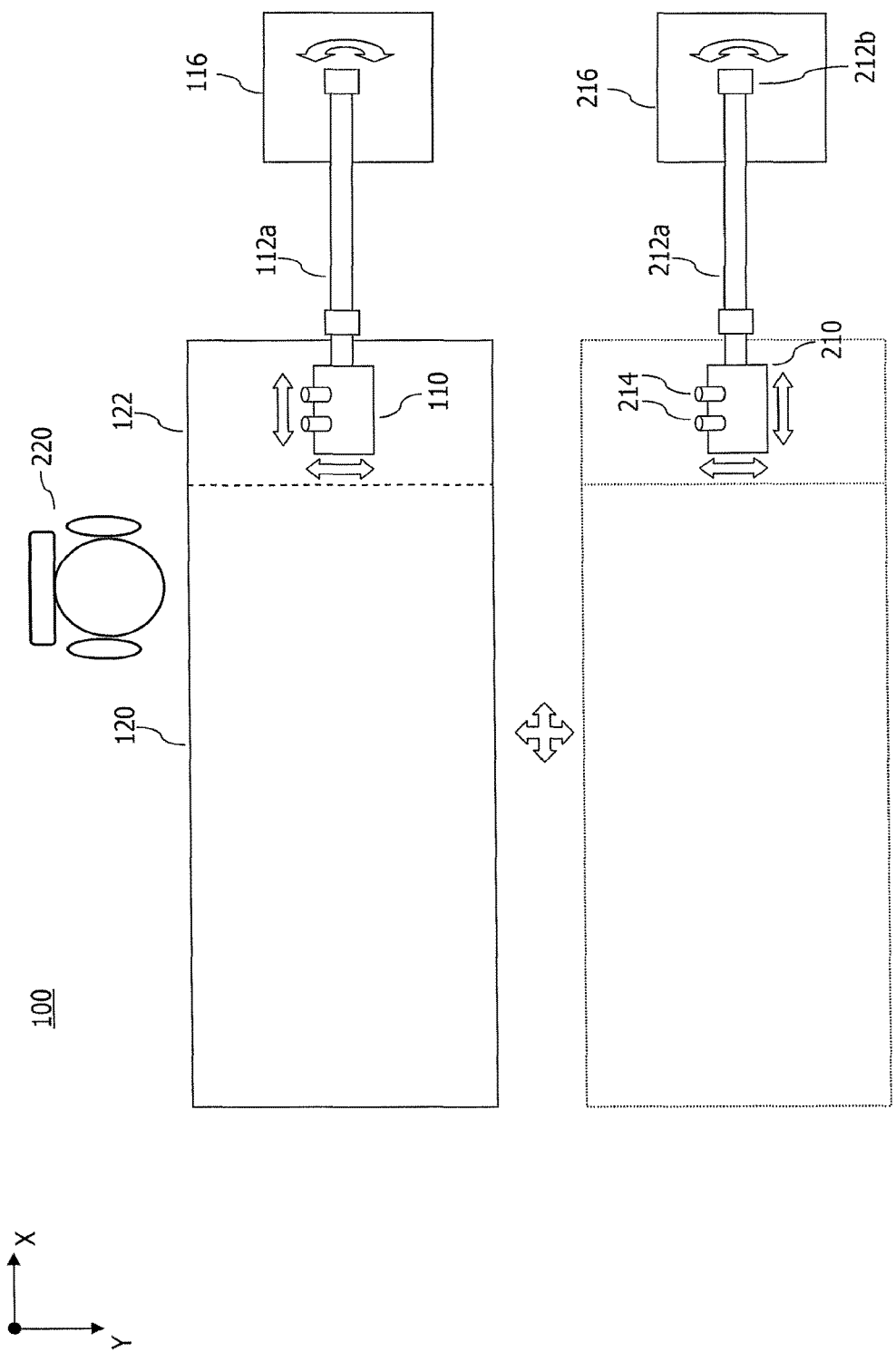
Figure 3:
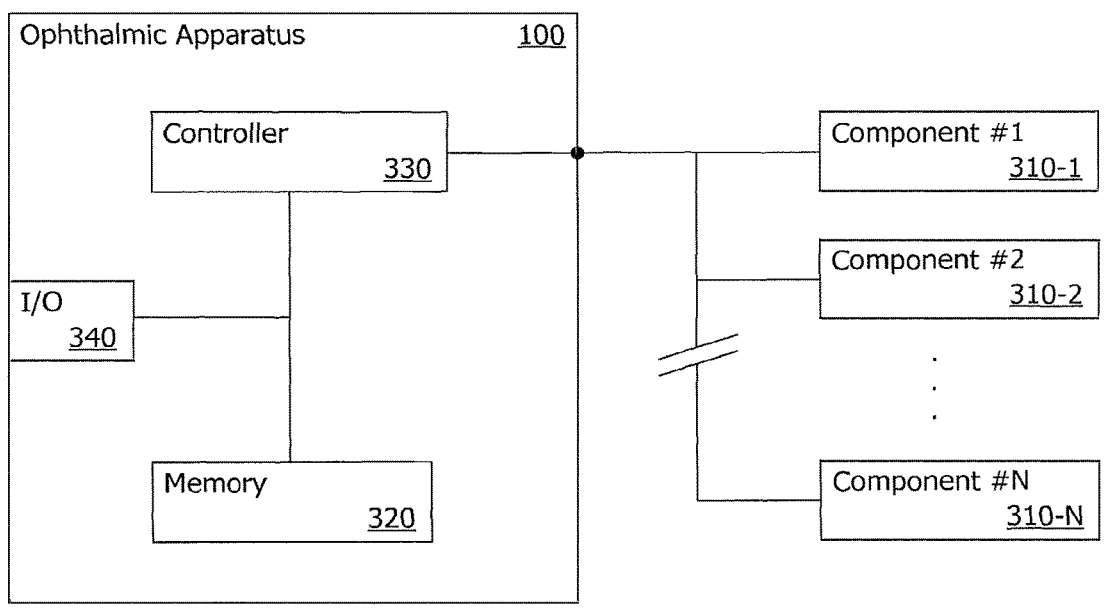

Embodiments of the present invention will be described in more detail below with reference to the attached drawings, in which:

FIG. 1 illustrates a side view of a possible arrangement of components of an ophthalmic apparatus according to an embodiment, FIG. 2 shows a top view of a further arrangement of components of an ophthalmic apparatus according to an embodiment, FIG. 3 illustrates schematically the elements of an ophthalmic apparatus for adjusting components according to an embodiment.

DETAILED DESCRIPTION OF THE DRAWINGS

An ophthalmic apparatus can be any medical device used by an ophthalmologist. It allows performing one or more procedures with respect to an eye of a patient, such as an eye-surgical, therapeutic and diagnostic procedure. Ophthalmic devices include, for example, a microscope or other optics to examine the human eye, or a laser device including a laser source, focusing optics, scanning components etc., which may be used in a LASIK (Laser-Assisted in-situ Keratomileusis) treatment. Such laser devices may include a femtosecond, picosecond, or attosecond laser or an excimer laser.

A conventional ophthalmic apparatus may have a disadvantage in that a tall person (e.g., an ophthalmologist) may have an uncomfortable posture standing at the ophthalmic apparatus during the entire procedure. Also, a short person may experience difficulties operating the ophthalmic apparatus.

An example arrangement of an ophthalmic apparatus 100 according to an embodiment of the present invention is illustrated in FIG. 1. The ophthalmic apparatus 100 includes a set of one or more configurable components allowing to adjust the configuration of apparatus 100 to the needs or preferences of a specific user of apparatus 100.

According to an embodiment, the set of configurable components include at least one illumination device (not shown) for providing illumination to a site of operation or examination of a patient eye undergoing a surgical/diagnostic/therapeutic procedure.

The illumination device may include, e.g., a ceiling-mounted lamp, a wall-mounted lamp, or a lamp supported on a base of apparatus 100.

The brightness of illumination light provided by the illumination device(s) is adjustable. The adjustable brightness allows the user of the ophthalmic apparatus, e.g., an ophthalmologist, to see well at each phase of the eye-surgical, therapeutic and diagnostic procedure.

In embodiments, the set of configurable components may include one or more position-variable components. A position of each position-variable component can be adjusted within any direction and dimension. That is, a position-variable component can be brought to any horizontal position, vertical position and/or angular position. The adjustment of a position-variable component of the ophthalmic apparatus 100 is illustrated in FIG. 1 by corresponding double arrows. The adjustment can be performed manually or controlled. For a controlled adjustment the position-variable component includes an actuator, such as a motor or servo.

An exemplary configurable component is an ophthalmic device 110. The ophthalmic device 110 is attached to a configurable or position-variable component, such as a movable arm 112. The arm 112 allows moving the ophthalmic device 110 in any of an X-, Y- or Z-direction. At least the movement in the Z-direction is necessary to bring a focussing optic of the ophthalmic device to the eye of the patient. FIG. 1 illustrates the movement in the X- and Z-direction by depicting corresponding double-arrows.

The arm 112 can also include position-variable members, e.g., an arm 112a and a base arm 112b. These arms allow the ophthalmic device 110 to be adjusted up and down, i.e. on the Z-axis, as well as to the left and to the right, i.e. on the X- and Y-axes. This provides a great flexibility for adjusting the position of the ophthalmic device 110 with respect to the patient and/or the ophthalmologist.

Although not illustrated in FIG. 1, the adjustment of the position of the ophthalmic device 110 as well as its corresponding arms 112a and 112b can be accomplished by suitable mechanisms, such as hydraulic piston(s), threaded spindle(s) or the like. Each of these adjusting mechanisms can be moved manually or automatically. For automatic movement a corresponding actuator, such as a motor, servo or the like, is integrated within the component.

Another configurable component is the stand at which the arm 112 is mounted. The arm 112 and stand 116 can be rotatably coupled, so that the arm and ophthalmic device 110 can swing. This allows adjusting the angular position of the ophthalmic device 110 around the stand 116.

The ophthalmic device 110 itself can include configurable components or configurable members. Such components or members comprise a microscopic device or microscope 113 with a pair of eyepieces 114 allowing the ophthalmologist to examine the eye of the patient or to perform a laser surgery at the eye of the patient. The microscopic device 113 is configurable in that a zoom factor and/or the focussing can be adjusted. Another configurable member is a lens. If more than one lens is present, they can be changed manually or automatically, for example, by revolving a plate on which the lenses are mounted.

At least one of the pair of eyepieces 114 is position-variable with respect to the other eyepiece of the pair to vary the mutual distance between the pair. As illustrated in FIG. 1, at least one eyepiece 114 can be adjusted in the X-direction. This adjustment of the eye pieces 114 allows adapting the ophthalmic device 110 to the distance of the eyes of the operator, such as a surgeon.

A further configurable member of the ophthalmic device 110 is a radiation emission head 118 for emitting optical radiation towards the patient's eye. The radiation emission head 118 is height-variable, i.e. the vertical position of the head can be adjusted. This vertical adjustment can be made within a predefined coordinate system or in relation to another configurable component or member, such as a resting surface of a resting member 120.

In an alternative configuration, the ophthalmic device 110 may not be attached to a stand 116 at the floor, but rather be mounted to a wall or ceiling of the operation room. This mounting can also be achieved by a rotatable coupling.

Moreover, the arm 112 holding the ophthalmic device 110 may be structured differently, for example, having more joints and respective arm pieces (112a, 112b) to increase the flexibility of adjusting the position of the ophthalmic device 110. In addition, an ophthalmic apparatus includes a resting member 120 providing rest for a human patient. The resting member is variable for at least one of a height of a resting surface of the resting member, a horizontal position of the resting surface and an inclination of the resting surface, wherein the controller is configured to adjust at least one of the height, horizontal position and inclination of the resting surface in accordance with the accessed user profile data.

Such resting member 120 can be a chair, bed or examination table 120 on which a patient rests, e.g., sits or lies, during an ophthalmological procedure or treatment. The position of resting member 120 can be adjusted up and down, i.e. in the Z-direction. This adjustment can be accomplished by a manually operated or motor-driven scissor mechanism 124 installed beneath the resting member 120. It is to be noted, that the present disclosure is not restricted to a scissor mechanism 124. The adjustment of the resting member can also be accomplished by a hydraulic or pneumatic system, a threaded spindle system, a retainer key technique or a tackle structure.

The resting member 120 can also provide a head part 122 on which the patient's head rests. This head part 122 is adjustable relative to the main part of the resting member 120. It can be adjusted via a variable inclination, for example, by swivelling the head part 122 against the main part.

Referring now to FIG. 2, a top view of a similar arrangement as illustrated in FIG. 1 is depicted. The ophthalmic apparatus as shown in FIG. 2 includes further configurable components.

These are an additional ophthalmic device 210, which can be a different laser device or an eye examination device, diagnosis device, etc. . . . The ophthalmic device 210 is also attached to a stand 216 via arms 212a and 212b in a similar manner as described above with respect to the ophthalmic device 110 (FIG. 1). The ophthalmic device 210 can also be mounted to a wall or ceiling while the structure 212 holding the device 210 can include any number of arms, joints or other structural elements. Further, the ophthalmic device 210 can also include position-variable components, such as two eyepieces 214, which can be adjusted in accordance with the distance of the eyes of an operator. That is, the eye pieces 214 can be adjusted in the illustrated X-direction.

As depicted in FIG. 2 with double arrows, each of ophthalmic devices 110 and 210 can be adjusted in the Y-direction as well as in the X-direction. This may comprise an adjustment of the angular position of the respective arms 112 and 212 due to a circular movement of the arms 112 and 212 against the stand. Thus, the ophthalmic devices 110 and 210 can be brought into any position above the resting member 120.

In order to allow the patient to enter the resting member 120 easily, the ophthalmic devices 110 and/or 210 can be moved away from the resting member 120. Alternatively, the resting member 120 can be adjusted in the X- and Y-direction as indicated by the double arrows. In this manner, the space above the resting member is not blocked by the ophthalmic devices 110 and 210 or other components such as the arms 112 and 212.

Some eye treatments, such as the LASIK treatment, may require that the patient is treated by two different devices subsequently. Therefore, the patient needs to stand up from one resting member and moves to another resting member associated with the second ophthalmic device. In accordance with the present disclosure, the resting member 120 can be adjusted in the X- and Y-direction, so that the patient can stay on the resting member while it is moved to the next ophthalmic device.

The ophthalmic apparatus may additionally include a chair or stand 220 for the ophthalmologist. This component 220 can also be adjusted in each direction (i.e. X-, Y- and Z-direction). This adjustment can be accomplished by similar techniques as described above for the resting member 120, such as hydraulic/pneumatic mechanisms, a thread spindle mechanism, etc.

The adjustment of the operator chair 220 has the advantage that the operator can have the most comfortable position with respect to the patient on the resting member 120 and/or the eye pieces 114 and 214 of the respective ophthalmic devices 210 and 220.

It is now referred to FIG. 3 schematically illustrating an ophthalmic apparatus according to the present disclosure.

As described above with respect to FIGS. 1 and 2 the ophthalmic apparatus 100 comprises a plurality of configurable components 310-1, 310-2 to 310-$n$ (also referred to as component(s) 310). Each of the components 310 refers to one of the configurable components described above. For example, component 310-1 can be the ophthalmic device 110, while component 310-2 refers to the resting member 120. As will be understood by the person skilled in the art, this designation of the components is exemplary only. According to another example, the component 310-2 could also refer to one of the arms 112a and 112b.

Referring back to FIG. 3, ophthalmic apparatus 100 comprises a memory 320, a controller 330 and a user interface device 340.

The controller 330 is configured to request log-in data from an operator of the ophthalmic apparatus 100. This log-in data request can be accomplished by using the user interface device 340 or input/output (I/O) interface 340, such as a screen, keyboard, mouse, touchscreen, touch pad, smart-card reader, fingerprint scanner or the like.

The user then logs in with the controller of the ophthalmic apparatus, e.g., by providing a user name or user identifier and, optionally, a password. Other forms of user identification can be implemented by a smart card storing user identification data in a secure format or a biometric scan (e.g., a fingerprint scan).

After provision of the log-in data by the user, the controller 330 determines whether a user profile is stored in memory 320 for the particular user. The controller 330, therefore, searches for a corresponding user profile in memory 320. This can be accomplished by extracting the user name, user identifier or other identifier of the user from the input log-in data and comparing it with corresponding identifiers of user profiles stored in memory 320.

If a matching user profile is found, the controller accesses and retrieves user profile data from memory 320. Such user profile data comprises configuration data specific for the identified user. The configuration data represents adjustment parameter/value-pairs for configurable components customized for the respective user as will be explained in more detail below. The configuration data, for example, consists of setting options for the configurable components and corresponding parameter values.

If there is no user profile for the retrieved log-in data stored in memory 320, the controller provides a message to the user, for example, via the I/O interface 340, whether the user wants to create a new user profile. If a new profile is created and stored in memory 320, a default configuration is retrieved from memory 320 or another non-volatile storage (not shown).

The storage of one or more user profiles associated with respective operators (users) of the ophthalmic apparatus 100 allows the customization of each configurable component of the ophthalmic apparatus. For instance, if the ophthalmic apparatus is installed in a clinic, hospital or medical practice, where a plurality of people uses the ophthalmic apparatus, a user profile for each user or operator of the ophthalmic apparatus can be stored in memory 320. This user profile may be identified by log-in data, such as a name or identifier of the user and an optional password.

The configuration data of each user profile corresponds to a data set. The configuration data may consist of one or more parameter/value-pairs for particular setting options of the configurable components.

A parameter may represent a setting option for one of the configurable components 310. The setting option or parameter may be the position of the component or a height of the component in the X-Y-Z-space or other coordinate system. The position and height of the component refers to a particular location of a point, for example, on a surface of the component in the X-Y-Z-space or other coordinate system. A setting option may therefore refer to one of the three directions (axes). A corresponding parameter value is then, for example, a coordinate within the X-Y-Z-space.

Alternatively, a component 310 may have a particular position of origin or zero-position. A parameter value for each of the three dimensions could then be an offset from this zero-position. For example, the parameter value could be −2/−1/0/+1/+2 cm/mm offset from the zero-position. As it will be understood, any other number of offset variations and any unit for these distances are also possible parameter values and therefore fall within the scope of the present disclosure.

Additionally or alternatively, a parameter value may also represent a relative distance to another component 310. For instance, a parameter may represent the mutual distance of two eyepieces of a microscope. Another parameter may represent the mutual distance between the ophthalmic device 110, 210 and the resting surface of the resting member 120. Thus, if the resting member is adjusted, the ophthalmic device 110, 210 will be adjusted correspondingly.

Depending on the component 310, a setting option can also be an angle of the component with respect to a particular line or plane, the focus or zooming of an optic element, a power intensity of a laser device, and/or the brightness of an illumination device.

In case the component 310 is the resting member 120 or the operator chair or stand 220, one parameter may represent the setting of the height, i.e. the position of the resting surface or top surface of the seating area in the Z-direction.

Additional components according to the present disclosure include graphical user interfaces of the ophthalmic apparatus 100. For instance, the arrangement of windows, applications or programs on a screen, the illustration of lists, masks or other information displayed, particular patient information, a system or component condition, etc. can be regarded as a configurable component. The apparatus 100 according to the present disclosure is capable of storing parameters of these components to also customize the graphical user interfaces for each logged-in user. Thus, the parameter values of each component, i.e. configuration data, for a particular user can be stored in a memory 320 of the ophthalmic apparatus 100. The controller 330 accesses in or retrieves from the memory 320 the parameter values of the configuration data and configures the component(s) 310 accordingly. After an optional processing of the configuration data, the controller 330 transmits control signals to the respective component 310-1, 310-2, etc., in order to adjust a horizontal, vertical or angular position, a height, an inclination, a distance, an optical factor, a power value or brightness. Each component 310 can include an interface (not shown) to receive the control signal. A corresponding actuator or other adjusting mechanism adjusts the component in correspondence with the control signal from controller 330.

In this manner, the ophthalmic apparatus can be used by a plurality of operators. Each time an operator logs into the system, the controller 330 of ophthalmic apparatus 100 automatically adjusts all components in a manner suitable to the logged-in operator. Thus, the ophthalmic apparatus 100 is fully customizable. As an example only, if a user wants to store a certain position of the examination table 120 and the ophthalmic device 110 within the X-Y-Z-space, the memory 320 would store six parameter values, i.e. three coordinate values for each component, together with the user profile of the respective user. If further components are necessary to achieve the certain position (such as the arms 112a, 112b), then the number of parameters increases. However, the present disclosure is not limited to coordinate values as already noted above. In case that the parameters do not relate to a coordinate value, but to an offset value for the configurable component, the memory 320 may only store offset values, i.e. parameter values, for setting options that are not zero. In other words, if a particular configurable component shall only be offset 5 cm from a zero-position, it is sufficient to only store this offset value for the corresponding direction (axis) for this particular component together with the corresponding user profile in memory 320.

In accordance with the present disclosure, the operator is relieved from the burden of adjusting each of the components separately, so that he or she can work in a comfortable position and familiar environment. Thus, the ophthalmic apparatus in accordance with the present disclosure provides a login procedure, after which each configurable component is automatically brought into a configuration which is comfortable for the logged-in operator and where each configurable component fulfils the needs of the respective operator.

The invention claimed is:

1. An ophthalmic apparatus, comprising:
   a resting member configured to provide rest for a human patient;
   an ophthalmic device configured to perform one or more procedures with respect to an eye of the patient resting on the resting member, the one or more procedures including at least one of an eye-surgical, therapeutic and diagnostic procedure;
   a user interface device configured to receive log-in data from a user; and
   a controller configured to: access stored user profile data based on the log-in data, the user profile data comprising configuration data specific for the user, the configuration data representing adjustment parameter/value-pairs for customizing one or more configurable components of the apparatus specifically for the user: and
   configure the one or more configurable components of the apparatus using the configuration data of the accessed user profile data.

2. Wherein the one or more configurable components include an illumination device, wherein the controller is configured to adjust the brightness of illumination light provided by the illumination device in accordance with the accessed user profile data.

3. The ophthalmic apparatus of claim 1, wherein the one or more configurable components include one or more position-variable components, wherein the controller is configured to adjust a position of at least one of the one or more position-variable components in accordance with the accessed user profile data.

4. The ophthalmic apparatus of claim 3, wherein the position includes at least one of a horizontal position, a vertical position and an angular position.

5. The ophthalmic apparatus of claim 3, wherein the one or more position-variable components include the resting member, wherein the resting member is variable for at least one of a height of a resting surface of the resting member, a horizontal position of the resting surface and an inclination of the resting surface, wherein the controller is configured to adjust at least one of the height, horizontal position and inclination of the resting surface in accordance with the accessed user profile data.

6. The ophthalmic apparatus of any of, claim 3 wherein the one or more position-variable components include one or more position-variable members of the ophthalmic device, wherein the controller is configured to adjust a position of at least one of the one or more position-variable members in accordance with the accessed user profile data.

7. The ophthalmic apparatus of claim 6, wherein the ophthalmic device is equipped with a microscope having a pair of eyepieces, wherein at least one of the pair of eyepieces is position-variable with respect to the other eyepiece of the pair to vary the mutual distance between the pair, wherein the controller is configured to adjust the mutual distance between the pair of eyepieces in accordance with the accessed user profile data.

8. The ophthalmic apparatus of claim 6, wherein the ophthalmic device is equipped with a radiation emission head for emitting optical radiation toward the patient eye, wherein the radiation emission head is height-variable, wherein the controller is configured to adjust the height of the radiation emission head in accordance with the accessed user profile data.

9. The ophthalmic apparatus of claim 8, wherein the radiation emission head is height-variable relative to the resting surface of the resting member, wherein the controller is configured to adjust the height of the radiation emission head in relation to the resting surface in accordance with the accessed user profile data.

10. A method of configuring an ophthalmic apparatus including at least a resting member providing rest for a human patient, an ophthalmic device for performing one or more procedures with respect to an eye of the patient resting on the resting member, the one or more procedures including at least one of an eye-surgical, therapeutic and diagnostic procedure, and a user interface device, the method comprising: receiving log-in data from a user on the user interface device; accessing stored user profile data based on the log-in data, the user profile data comprising configuration data specific for the user, the configuration data representing adjustment parameter/value-pairs for customizing one or more configurable components of the apparatus specifically for the user; and configuring the one or more configurable components of the ophthalmic apparatus in using the configuration data of the accessed user profile data.

11. The method of claim 10, wherein the one or more configurable components include an illumination device, wherein configuring comprises adjusting the brightness of illumination light provided by the illumination device in accordance with the accessed user profile data.

12. The method of claim 10, wherein the one or more configurable components include one or more position-variable components, wherein configuring comprises adjusting a position of at least one of the one or more position-variable components in accordance with the accessed user profile data.

13. The method of claim 12, wherein the one or more position-variable components include the resting member, wherein the resting member is variable for at least one of a height of a resting surface of the resting member, a horizontal position of the resting surface and an inclination of the resting surface, wherein configuring comprises adjusting at least one of the height, horizontal position and inclination of the resting surface in accordance with the accessed user profile data.

14. The method of claim 12, wherein the one or more position-variable components include one or more position-variable members of the ophthalmic device, wherein configuring comprises adjusting a position of at least one of the one or more position-variable members in accordance with the accessed user profile data.

15. The method of claim 14, wherein the ophthalmic device is equipped with a radiation emission head for emitting optical radiation toward the patient eye, wherein the radiation emission head is height-variable, wherein configuring comprises adjusting the height of the radiation emission head in accordance with the accessed user profile data or adjusting the height of the radiation emission head in relation to the resting surface of the resting member in accordance with the accessed user profile data.

* * * * *